US00PP09219P

United States Patent [19]

Trees

[11] Patent Number: Plant 9,219

[45] Date of Patent: Jul. 25, 1995

[54] GERANIUM PLANT NAMED BFP-420 BRIGHT RED

[75] Inventor: Scott C. Trees, Arroyo Grande, Calif.

[73] Assignee: Geo. J. Ball, Inc., West Chicago, Ill.

[21] Appl. No.: 341,912

[22] Filed: Nov. 15, 1994

[51] Int. Cl.[6] ..... A01H 5/00
[52] U.S. Cl. ..... Plt./87.12
[58] Field of Search ..... Plt. 87.12

[56] References Cited

U.S. PATENT DOCUMENTS

P.P. 7,959 9/1992 Hanes ..... Plt./87.12
P.P. 8,053 12/1992 Hoffmann ..... Plt./87.12

*Primary Examiner*—James R. Feyrer
*Attorney, Agent, or Firm*—Burns, Doane, Swecker & Mathis

[57] ABSTRACT

A new and distinct *Pelargonium*×*hortorum* cultivar named BFP-420 Bright Red is provided. This new Zonal Geranium cultivar was the result of a controlled breeding program wherein a plant designated BFP-56 (non-patented in the United States) was pollinated by a plant designated 3113D. The new plant forms attractive dark red semi-double florets and medium green foliage with attractive zonation. A medium self-branching growth habit is exhibited in the absence of a growth regulator.

1 Drawing Sheet

SUMMARY OF THE INVENTION

The present invention comprises a new and distinct Geranium cultivar, botanically known as *Pelargonium*-×*hortorum* Bailey, and hereinafter is referred to the cultivar named BFP-420 Bright Red.

The new cultivar is the product of a planned breeding program which had as its objective the creation of a new Geranium cultivar that exhibits uniform flowers, medium green foliage, a medium self-branching growth habit that requires no growth regulator, a propensity for rapid rooting, and a stable foliage coloration during shipment.

The breeding program that resulted in the production of the new cultivar of the present invention was carried out during 1989 at Arroyo Grande, Calif., U.S.A. The female parent (i.e., seed parent) was plant designated BFP-56 (non-patented in the United States) which exhibits semi-double red florets with light green foliage. The male parent (i.e., pollen parent) was a plant designated 3113D (non-patented in the United States) which exhibits semi-double dark red florets and medium green foliage with a distinct zone. The parentage of new BFP-420 Bright Red cultivar can be summarized as follows:

BFP-56×3113D.

BFP-420 Bright Red was discovered and selected during 1990 as a highly distinctive flowering plant from among the progeny of the stated cross at Arroyo Grande, Calif., U.S.A. This plant was initially designated BFP-420.

It was found that the new cultivar of the present invention:

(a) exhibits attractive dark red semi-double florets,
(b) forms medium green foliage with zonation, and
(c) exhibits a medium self-branching growth habit in the absence of a growth regulator.

When plant material of the BFP-420 Bright Red cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of BFP-420 Bright Red was accomplished when vegetative cuttings were taken from the initial selection in a controlled environment at Arroyo Grande, Calif., U.S.A. by a technician working under the direction and supervision of the originator of the new cultivar. Horticultural examination of plants resulting from such asexual propagation during 1990 has demonstrated that the combination of characteristics as herein disclosed for the BFP-420 Bright Red cultivar are firmly fixed and is retained through successive generations of such asexual reproduction.

The new BFP-420 Bright Red cultivar has not been observed under all possible environmental conditions. Accordingly, the described phenotype may vary somewhat with variations in the environment, such as temperature, light intensity, and day length.

Of the many commercially available Geranium cultivars, the Sassy Dark Red cultivar (U.S. Plant Pat. No. 8,053) is considered to be most similar to the new BFP-420 Bright Red cultivar. When the new cultivar of the present invention is compared to the Sassy Dark Red cultivar, the BFP-420 Bright Red cultivar exhibits smaller umbels, (e.g., approximately 9.0 to 9.5 cm.×6.0 to 6.2 cm. vs. approximately 9.5 to 11.0 cm.×6.0 to 7.0 cm.), more florets per umbel (e.g., approximately 39 to 41 vs. 30 to 37), and more petaloids per floret (e.g., 2 to 3 vs. 1 to 2).

The new cultivar of the present invention is being marketed by Geo. J. Ball, Inc. under the Designer trademark.

BRIEF DESCRIPTION OF THE PHOTOGRAPH

The accompanying photograph shows a typical plant of the new BFP-420 Bright Red cultivar with colors being as nearly true as it is reasonably possible to make the same in a color illustration of this character. Typical flowers and foliage are depicted. The plant was grown in a greenhouse at West Chicago, Ill., U.S.A.

DETAILED DESCRIPTION

The following observations, measurements and comparisons describe plants grown in Ball FloraPlant's greenhouses at West Chicago, Ill., U.S.A. under conditions which approximate those generally used in commerical practice. In the following description, color references are made to The R.H.S. Colour Chart of The Royal Horticultural Society, London, England. The color values were determined between 9:00 and 10:00 a.m. on Jul. 21, 1994, under natural light conditions of 2,000 footcandles.

Classification:

*Botanical.* ×*Pelargonium*×*hortorum* Bailey, cv. BFP-420 Bright Red.

*Commerical.*—Zonal Geranium.

Inflorescence

A. Umbel:

*Average diameter.*—Approximately 9.0 to 9.5 cm. compared to approximately 9.5 to 11.0 cm. for the Sassy Dark Red cultivar.

*Average depth.*—Approximately 6.0 to 6.2 cm. compared to approximately 6 to 7 cm. for the Sassy Dark Red cultivar.

*Penduncle length.*—Approximately 16.5 to 19.5 cm. compared to approximately 16 to 18 cm. for Sassay Dark Red cultivar.

*Pedical length.*—Approximately 2.7 to 3.2 cm. compared to approximately 3.0 to 3.4 cm. for the Sassy Dark Red cultivar.

*Number of umbels/plant.*—When grown in a 10 cm. pot at 9 weeks after the sticking of a rooted cutting, there commonly are approximately 3 to 5 umbels per plant. This compares to approximately 4 to 5 umbels per plant for the Sassy Dark Red cultivar. When plants are grown in the field for 16 weeks, the new cultivar commonly possesses approximately 10 umbels per plant while the Sassy Dark Red cultivar commonly possesses approximately 14 umbels per plant.

*Number of florets/umbel.*—When grown in 10 cm. pots, approximately 39 to 41 florets per umbel commonly are formed at 9 weeks whereas plants of the Sassy Dark Red cultivar grown in the same manner commonly exhibit approximately 30 to 37 florets per umbel.

Corolla:

*Average diameter.*—Approximately 5.0 to 5.1 cm. compared to approximately 4.7 to 5.1 cm. for the Sassy Dark Red cultivar.

*Form.*—Semi-double for both the BFP-420 Bright Red and the Sassy Dark Red cultivars.

*Number of petaloids.*—Commonly 2 to 3 petaloids per floret are formed whereas the Sassy Dark Red cultivar commonly possesses only 1 to 2 petaloids per floret.

*Color.*—General tonality from a distance of three meters: Red. Adaxial: Red Group 44B compared to Red Group 46B for the Sassy Dark Red cultivar. Abaxial: Red Group 43B for Bright Red and Red Group 46C for the Sassy Dark Red cultivar.

C. Bud:

*Shape.*—Oval.

*Color.*—Adaxial: Red Group 44B compared to Red Group 46B for the Sassy Dark Red cultivar. Abaxial: Red Group 43B compared to Red Group 46C for the Sassy Dark Red cultivar.

D. Reproductive organs:

*Androecium.*—The anthers are commonly approximately 2 mm. in length. The pollen color is Orange-Red Group 31A for both the BFP-420 Bright Red and the Sassy Dark Red cultivars. The filaments, which are sometimes petaloid, are approximately 4 to 7 mm. in length compared to approximately 3 to 7 mm. for the Sassy Dark Red cultivar.

*Gynoecium.*—The pistil length commonly is approximately 10 mm. There is a single stigma which commonly has a length of approximately 5 mm. which commonly branches into 5 parts, and the style length commonly is approximately 5 mm.

*Fertility.*—Usually does not produce fruits in the absence of mechanical fertilization.

E. Spring Flowering Response Period: Approximately 6 to 7 weeks from rooted cuttings under greenhouse conditions.

F. Outdoor flower production: Freely flowering under outdoor growing conditions with substantially continuous blooming.

G. Durability: Ships well.

Plant

A. Foliage: Medium green with zone.

*Form.*—Reinform, with cordate base.

*Margin.*—Crenate.

*Color.*—Adaxial: Yellow-Green Group 147A with a zone of Yellow-Green Group 146A compared to Yellow-Green Group 147A for the Sassy Dark Red cultivar. Abaxial: Yellow-Green Group 147B compared to Yellow-Green Group 147C for the Sassy Dark Red cultivar.

*Size.*—Approximately 8.1 to 8.4 cm. at the widest point and approximately 6.7 to 7.0 cm. at the narrowest points. This compares to approximately 8.3 to 8.8 cm. at the widest point and approximately 6.9 to 7.1 cm. at the narrowest point for the Sassy Dark Red cultivar.

*Tolerance of botrytis.*—Greater than many commercial red varieties.

B. General appearance and form:

*Internode length.*—Commonly varies from approximately 2.0 to 2.5 cm. compared to approximately 2.0 to 3.0 cm. for Sassy Dark Red cultivar.

*Branching pattern.*—Freely basal branching. No pinching is required to obtain self-branching.

*Height.*—Commonly approximately 28 to 29 cm. above a 10 cm. pot at 9 weeks under standard greenhouse conditions. This compares to approximately 25 to 27 cm. for the Sassy Dark Red cultivar under the same conditions.

What is claimed is:

1. A new and distinct Geranium plant named BFP-420 Bright Red, substantially as herein described and shown, which:

(a) exhibits attractive dark red semi-double florets,
(b) forms medium green foliage with zonation, and
(c) exhibits a medium self-branching growth habit in the absence of a growth regulator.

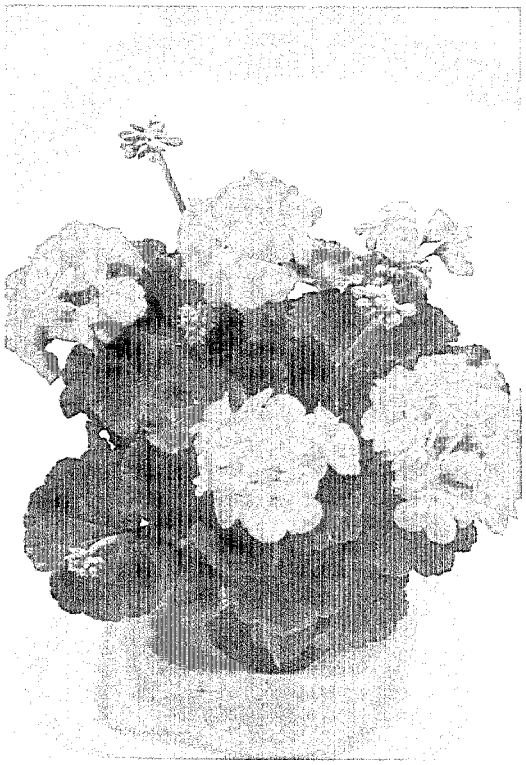

* * * * *